US008675949B2

(12) United States Patent  
Takagi et al.

(10) Patent No.: US 8,675,949 B2  
(45) Date of Patent: Mar. 18, 2014

(54) REVIEWED DEFECT SELECTION PROCESSING METHOD, DEFECT REVIEW METHOD, REVIEWED DEFECT SELECTION PROCESSING TOOL, AND DEFECT REVIEW TOOL

(75) Inventors: Yuji Takagi, Kamakura (JP); Minoru Harada, Fujisawa (JP); Yuichi Hamamura, Yokohama (JP)

(73) Assignee: Hitachi High-Technologies Corporation, Tokyo (JP)

( * ) Notice: Subject to any disclaimer, the term of this patent is extended or adjusted under 35 U.S.C. 154(b) by 234 days.

(21) Appl. No.: 13/266,800

(22) PCT Filed: Mar. 25, 2010

(86) PCT No.: PCT/JP2010/055173  
§ 371 (c)(1),  
(2), (4) Date: Dec. 28, 2011

(87) PCT Pub. No.: WO2010/125877  
PCT Pub. Date: Nov. 4, 2010

(65) Prior Publication Data  
US 2012/0093392 A1    Apr. 19, 2012

(30) Foreign Application Priority Data

Apr. 28, 2009  (JP) .................................. 2009-109284

(51) Int. Cl.  
    *G06K 9/00*         (2006.01)
(52) U.S. Cl.  
    USPC .............................. 382/145; 382/294; 716/55
(58) Field of Classification Search  
    USPC ..................... 382/145, 294; 716/55  
    See application file for complete search history.

(56) References Cited

U.S. PATENT DOCUMENTS

| 7,869,966 | B2* | 1/2011 | Okabe et al. ................... 702/82 |
| 2007/0048635 | A1* | 3/2007 | Schulze et al. ................. 430/30 |
| 2008/0008401 | A1* | 1/2008 | Zhu et al. ...................... 382/294 |
| 2008/0298669 | A1* | 12/2008 | Funakoshi et al. ............ 382/145 |
| 2009/0136121 | A1* | 5/2009 | Nakagaki et al. ............. 382/149 |
| 2010/0138801 | A1* | 6/2010 | Matsuoka et al. ............... 716/6 |

OTHER PUBLICATIONS

Ray Yen et al., Lithography Hotspot Discovery at 70nm DRAM 300MM Fab: Process Window Qualification Using Design Base Binning, PE-O-044, Dec. 2008.

Hisae Shibuya et al., Practical Pattern detection from Distributed Defect Points on a Semiconductor Wafer, MVA2002 IAPR workshop on Machine Vision Applications, Dec. 11-13, 2002, Nara-Ken New Public Hall, Nara, Japan.

* cited by examiner

*Primary Examiner* — Hadi Akhavannik  
(74) *Attorney, Agent, or Firm* — Antonelli, Terry, Stout & Kraus, LLP.

(57) ABSTRACT

The present invention relates to semiconductor inspection and provides a technology capable of efficiently detecting a systematic defect. In the present system, with regard to the process (S7, S8) of matching hot spot (HS) points that can be simulated in advance and defect points obtained as a result of a visual inspection each other and the unmatched defect points, a process (S6, S9) of classifying the defect points into groups based on similarity of pattern layout at the defect points to determine the defects belonging to a pattern layout where defects frequently occur, thereby reliably detecting the systematic defect. Also, with a process (S11) of acquiring an uneven distribution in a defect occurrence distribution on a wafer, the systematic defect occurring due to topography of the wafer can also be detected.

18 Claims, 10 Drawing Sheets

X: DEFECT POINT (COORDINATES)

○ : GROUP A
□ : GROUP B

FIG. 5A

○ : GROUP A
□ : GROUP B

◇ : GROUP C
△ : GROUP D

REVIEWED DEFECT SELECTION PROCESSING METHOD, DEFECT REVIEW METHOD, REVIEWED DEFECT SELECTION PROCESSING TOOL, AND DEFECT REVIEW TOOL

TECHNICAL FIELD

The present invention relates to semiconductor manufacturing and inspecting technologies, and more particularly to technologies of a reviewed defect selection processing method for selecting (sampling) a defect to be reviewed (reviewed defect) from defects detected in a visual inspection of a semiconductor wafer (detected defects). Furthermore, the present invention relates to technologies for reviewing defects with an emphasis on a systematic defect (defect occurring depending on the shape and design of pattern layout, device characteristics and others) due to exposure process, mask and other factors.

BACKGROUND ART

As for the defects detected in a visual inspection of a semiconductor wafer (detected defects), in order to review their details, a defect to be reviewed (reviewed defect) is selected (sampled) from the detected defects and is reviewed with a scanning electron microscope or the like.

Examples of prior art regarding a systematic defect among various types of defect are as follows.

Non-Patent Document 1 discloses a method in which a group of "position dependent repeat defects" present at the same place when seen per chip and a group of "pattern layout dependent repeat defects" present on the same pattern layout found by the search of pattern layout near the points of detected defects are extracted from among defects on a wafer that are obtained as a result of a visual inspection of a semiconductor wafer, these two groups are considered as candidates for systematic defects due to exposure process and mask, and then reviewed defects are sampled from these two groups.

PRIOR ART DOCUMENTS

Non-Patent Documents

Non-Patent Document 1: R. Yen, et al., "Lithography Hot Spot Discovery at 70 nm DRAM 300 mm Fab: Process Window Qualification Using Design Based Binning", PE-0-044, proc of International Symposium on Semiconductor Manufacturing 2008

Non-Patent Document 2: Hisae Shibuya, Yuji Takagi, Yasuo Nakagawa, "Defect Classification based on Pattern Recognition of Distributed Points", The Transactions of the Institute of Electrical Engineers of Japan, C, 127(4), pp. 521-527 (2007-4)

SUMMARY OF THE INVENTION

Problems to be Solved by the Invention

Systematic defects due to exposure process and mask occurring after resist coating, development or etching have become a problem with the scaling down of semiconductor circuit patterns. In order to detect these microscopic defects, a highly-sensitive visual inspection is required. As a result of such a highly-sensitive inspection, however, many defects including foreign substances, nuisance defects and misinformation are detected in addition to the systematic defects.

For this reason, there is a problem that even if the visual inspection is performed to check the state of exposure process, the systematic defects due to exposure process and mask may be buried in these many detected defects. In other words, there is a problem that it is difficult to discriminate and check whether individual detected defects (defect points in a map) obtained as a result of the visual inspection are systematic defects or other types of defects and others (defect types or the like).

Regarding the systematic defects, the method described in the Non-Patent Document 1 mentioned above (method in which the two groups described above are extracted, these groups are considered as candidates for systematic defects, and then reviewed defects are sampled) is known.

(1) However, the Non-Patent Document 1 does not disclose a method of checking whether the sampled defect points correspond to hot spots (Hot Spot: place that can be simulated in advance and has high probability of occurrence of systematic defects due to exposure process and the like). Therefore, the method described in the Non-Patent Document 1 has a problem that it is impossible to exhaustively check the hot spots that can be simulated in advance.

(2) Moreover, the Non-Patent Document 1 does not disclose a method of controlling a sampling position on a wafer in accordance with a defect distribution on the wafer, either. Therefore, the method described in the Non-Patent Document 1 has a problem that it is impossible to detect an uneven distribution of systematic defects on the wafer occurring due to topography of the wafer.

In view of the problems above, a main object or a major object of the present invention is to provide a technology capable of exhaustively and efficiently detecting systematic defects, and so forth.

(1) In detail, a first object among these is to be able to detect a defect due to a local pattern layout, which is a first factor (cause) for the defect. (1-1) A technology capable of reliably detecting a systematic defect occurring at a hot spot that can be simulated (expected) in advance is provided. (1-2) In addition, a technology capable of detecting also a hot spot (its corresponding systematic defect) that cannot be expected in a simulation in advance is provided.

(2) Furthermore, a second object (which is important next to the first object) is to provide a technology capable of detecting a defect (systematic defect) due to topography (characteristics) of the wafer, which is a second factor (cause) for the defect.

Means for Solving the Problems

The following is a brief description of an outline of the typical invention disclosed in the present application. (1) In the present invention, a processing unit which reliably matches hot spots that can be simulated in advance and detected defects obtained as a result of a visual inspection with each other is provided, and thus a process of exhaustively and efficiently detecting hot spots (their corresponding systematic defects) is performed. More specifically, this process includes a process of detecting systematic defects (first type of defects) corresponding to hot spots that can be expected in advance and a process of detecting systematic defects (second type of defects) corresponding to hot spots that cannot be expected in advance. (2) Also, in the present invention, a processing unit of acquiring an uneven distribution in defect occurrence distribution on a wafer is provided, and thus a process of detecting also a systematic defect occurring due to topography of the wafer is performed.

A reviewed defect selection processing method of the present embodiment is, for example, a reviewed defect selection processing method, in which based on information about a plurality of detected defects (defect group) outputted (detected) from a visual inspection tool (defect detector) which performs visual inspection targeted for a semiconductor wafer, a process of selecting (sampling) one or more reviewed defects (defects to be reviewed) for performing a detailed review from the plurality of detected defects is performed by using information processing of a computer.

This method includes: a process step of inputting information about positions (coordinates and others) of the plurality of detected defects from the visual inspection tool; a process step of inputting pattern layout data on a circuit board (chip and others) of the wafer (chip, shot and others); and a process step of performing a first process of classifying positions of the hot spots (appropriately abbreviated as HS) of the wafer calculated by a litho simulator into groups (for example, A to D) based on similarity of pattern layout and inputting information about the positions of the HS of each classified group. The litho simulator (simulator relating to exposure process, mask and others) calculates hot spots (places where possibility of occurrence of a systematic defect is estimated to be high) by simulation and outputs the information thereof.

Also, this method includes: a process step of discriminating (matching, determining) the plurality of detected defects between defects (K1) near the HS of the classified groups and defects (K2) not near the HS of the classified groups; a process step of performing a first grouping (G1) of the defects (K1) near the HS for each of the classified groups of the HS and selecting, from the defects subjected to the first grouping (G1), a reviewed defect for each of the classified groups; and a process step of performing a second process of classifying the positions of the defects (K2) not near the HS into groups based on similarity of pattern layout, performing a second grouping (G2) of the defects of each of the classified groups for each classified group, and selecting, from the defects subjected to the second grouping (G2), a reviewed defect for each classified group.

Also, the present embodiment includes: a process step of ascertaining a defect distribution area on the wafer for each of the classified groups (for example, A to D) in the first and second groupings (G1, G2); and a process step of selecting a reviewed defect from the ascertained area.

Further, the present embodiment includes: a process step of ascertaining a defect distribution area on a chip or a shot of the wafer for each of the classified groups in the first and second groupings; and a process step of selecting a reviewed defect from the ascertained area.

Furthermore, the present embodiment includes a process step of discriminating the detected defects between defects near the hot spots of the classified groups and defects not near the hot spots of the classified groups by representing the detected defects and the HS by chip coordinates or shot coordinates of the wafer and comparing the coordinates of the detected defects with the coordinates of the hot spots.

Also, a defect review method of the present embodiment includes a process step of acquiring an image for performing a detailed review of the reviewed defect based on information about the selected reviewed defect in addition to the process steps of the reviewed defect selection processing method described above.

With the configuration as described above, the HS obtained in advance in a simulation and the defect points obtained as a result of the visual inspection are matched with each other, whereby a systematic defect occurring at the HS can be reliably detected. Also, an uneven distribution in a defect occurrence distribution on a wafer is acquired, whereby a systematic defect occurring due to topography of the wafer and others can also be detected.

Effects of the Invention

The effects obtained by typical embodiments of the invention disclosed in the present application will be briefly described below. According to the present invention, systematic defects can be exhaustively and efficiently detected. (1) In detail, it is possible to detect a defect due to a local circuit pattern layout, which is a first factor for the defect. (1-1) It is possible to reliably detect a systematic defect occurring at a hot spot that can be simulated in advance. (1-2) In addition, it is possible to detect also a hot spot (its corresponding systematic defect) that cannot be expected in a simulation in advance. (2) Furthermore, it is also possible to detect a defect (systematic defect) due to topography (characteristics) of the wafer, which is a second factor for the defect.

BEST MODE FOR CARRYING OUT THE INVENTION

Hereinafter, embodiments of the present invention will be described in detail with reference to the accompanying drawings. Note that components having the same function are denoted by the same reference symbols throughout the drawings for describing the embodiments, and the repetitive description thereof will be omitted.

First Embodiment

A system of the first embodiment of the present invention will be described with reference to FIGS. 1 to 9. The reviewed defect selection processing tool and method according to the first embodiment represent an information processing unit 10 and a system (semiconductor inspection system) 100 including the information processing unit 10 of FIG. 1, and a method executed by the tool.

<Tool Configuration (1)>

Figure 1:
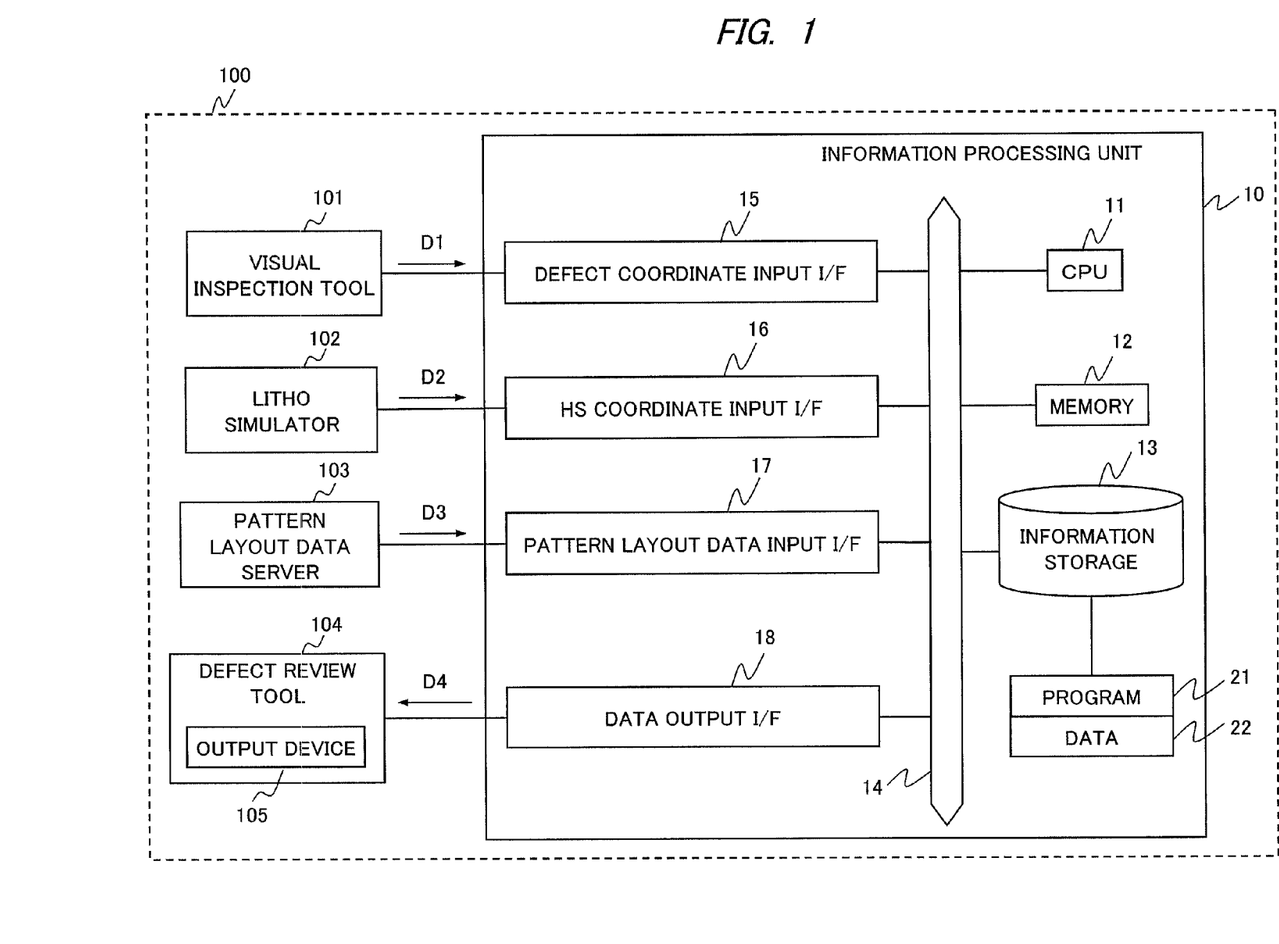
FIG. 1 is a drawing showing a system configuration according to the first embodiment of the present invention.

FIG. 1 depicts a tool configuration and others of the present system. A main device of the present system 100 is the information processing unit 10, and the information processing unit 10 is connected to a visual inspection tool 101, a litho simulator 102, a pattern layout data server 103, and a defect review tool 104. The information processing unit 10 includes a CPU 11, a memory 12, an information storage (HDD or the like) 13, a bus 14, a defect coordinate input I/F 15, an HS coordinate input I/F 16, a pattern layout data input I/F 17, and a data output I/F 18.

The information processing unit 10 performs information processing of the reviewed defect selection processing method by executing a program 21, by a dedicated circuit, or the like. For example, in the information storage 13, the program 21 and associated various data 22 are stored.

The visual inspection tool 101 is a visual inspection tool of a semiconductor wafer to be inspected. Information (defect coordinate data: D1) such as the coordinates of defects detected by a visual inspection in the visual inspection tool 101 is fed to the information processing unit 10 via the defect coordinate input I/F 15 (I/F: interface).

The litho simulator 102 models a light source, a lens, a mask and others of a lithography tool to simulate a mask transfer pattern onto the wafer and others (computing process by a program and others). Places where a process margin is small and defects tend to occur are calculated as Hot Spots (HS) by the litho simulator 102, and information about positional coordinates thereof (HS coordinate data: D2) is fed to the information processing unit 10 via the HS coordinate input I/F 16.

The pattern layout data server 103 holds data (pattern layout data: D3) including information about ideal pattern layout obtained by transferring a mask pattern onto the wafer (information about circuit (pattern) layout of the wafer, a chip, and others on a design basis), and the information data (D3) is fed to the information processing unit 10 via the pattern layout data input I/F 17.

The information data such as the defect coordinates (D1), the HS coordinates (D2), and the pattern layout (D3) fed to the information processing unit 10 is stored in the memory 12 or the information storage 13. Then, after the information data is read by the CPU 11 as appropriate and is subjected to processes depicted in FIG. 2 and following figures (selecting process and others), the information data as a result of these processes (that is, coordinates of selected defects to be reviewed) is again stored in the memory 12 or the information storage 13. Then, the information data as a final processing result (reviewed defect coordinate data: D4) is transferred via the data output I/F 18 to the defect review tool 104.

The defect review tool 104 includes an output device (display or the like) and performs processes of positioning the semiconductor wafer at a coordinate position of a review target defect and acquiring an image with a magnification suitable for reviewing that region based on the information data (D4) read from the information processing unit 10.

In the first embodiment, the information processing unit 10 can be regarded as a server which has a function of taking as inputs the defect coordinates (D1) from the visual inspection tool 101, the HS coordinates (D2) from the litho simulator 102, and the circuit pattern layout (D3) from the pattern layout data server 103 and a function of outputting the coordinates (D4) of the defect review points (review target defects) to the defect review tool 104.

<Process Flow (First Process Flow)>

Figure 2:
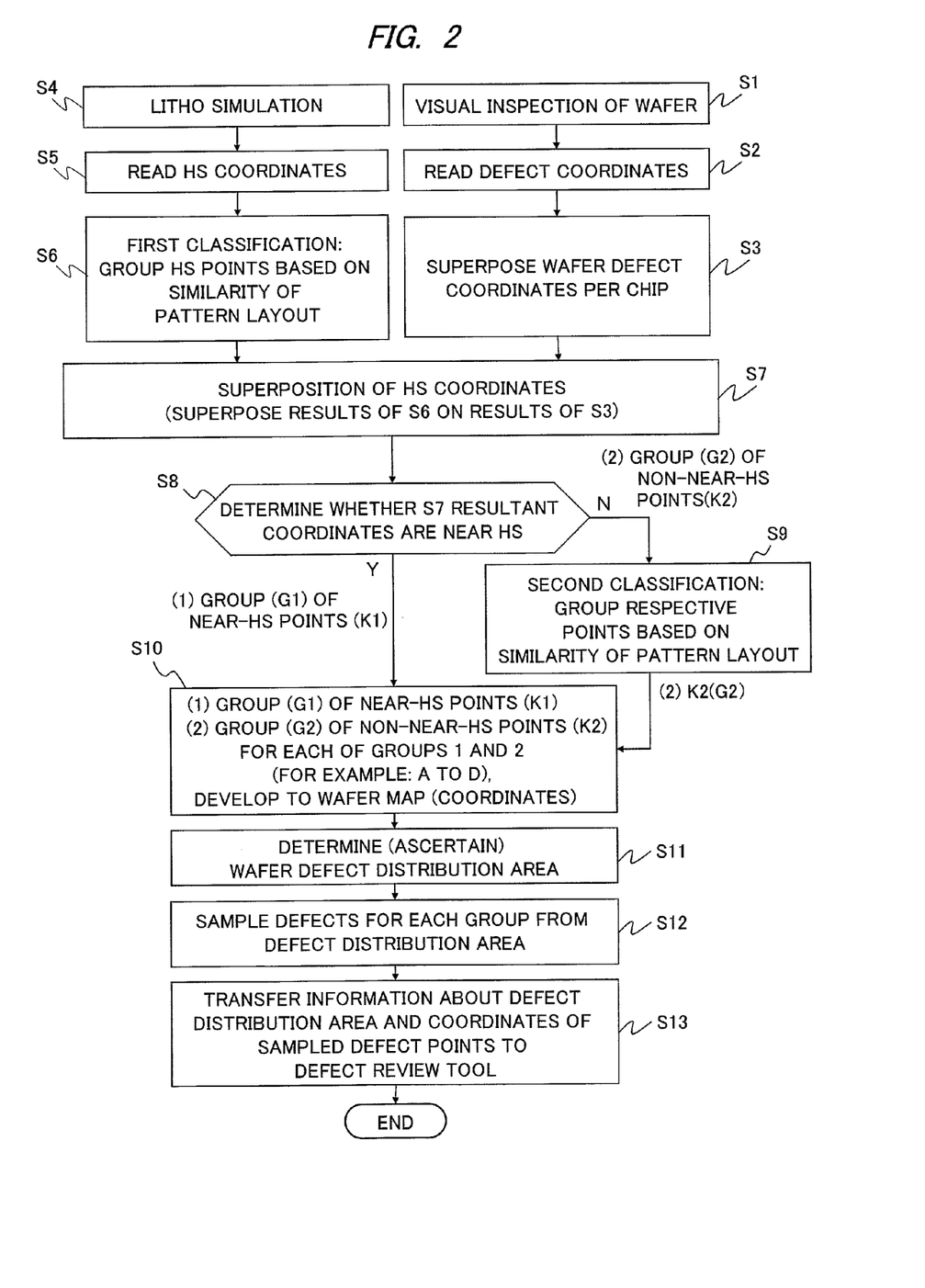
FIG. 2 is a drawing showing a process flow (first process flow) according to the first embodiment.

FIG. 2 depicts an entire process flow (first process flow) according to the present embodiment (S represents a process step).

<Process Flow (Visual Inspection)>

First, a visual inspection of a target wafer is performed by the visual inspection tool 101 (S1). Defect coordinates (D1) detected thereby are read into the information processing unit 10 (S2). Subsequently, a process of overlaying (superposing) the defect coordinates (D1) per chip is performed (S3). At S3, the defect coordinates are overlaid for all of the plurality of chips on the target wafer.

Figure 3:
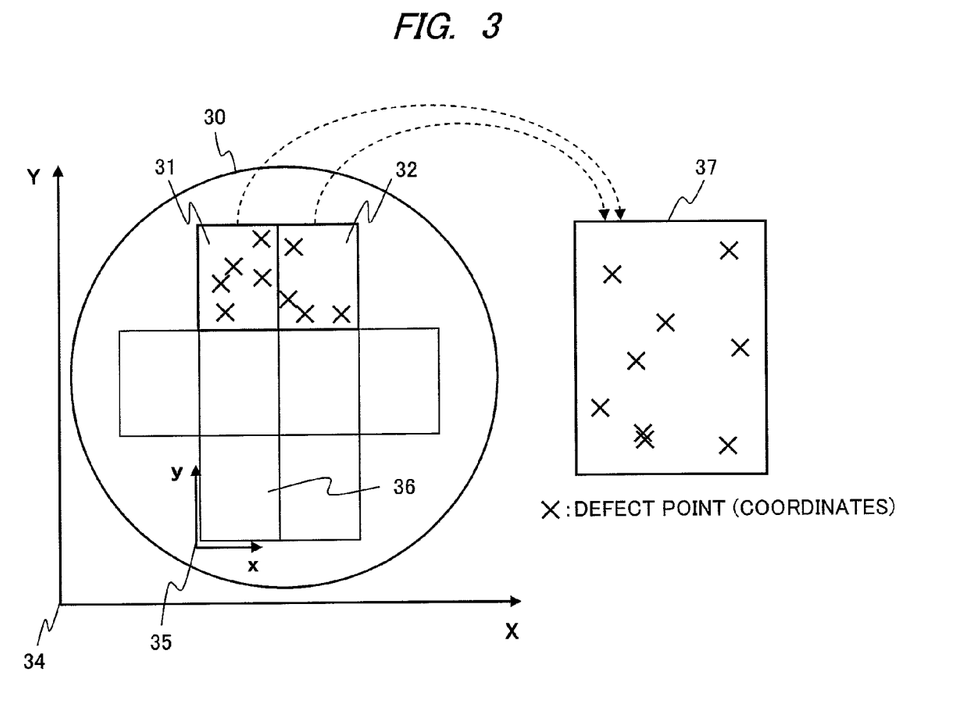
FIG. 3 is a drawing for describing a process (S3) of superposing a defect point in a wafer coordinate system onto a chip coordinate system in the first process flow.

The process of superposing the wafer defect coordinates per chip (for all chips) at S3 will be described with reference to FIG. 3. FIG. 3 schematically depicts that, for example, eight chips (denoted by 36 and others) are created on a target wafer 30. 34 denotes a wafer coordinate system for uniquely determining a position (coordinates or the like) on the wafer 30 (per wafer). On the other hand, 35 denotes a chip coordinate system for uniquely determining a position (coordinates or the like) on the chip 36 (per chip). The chip coordinate system 35 is allocated to each chip (that for only the chip 36 is shown in the drawing). Here, the wafer coordinate system 34 is represented by (X, Y) and the chip coordinate system 35 is represented by (x, y).

An origin of the chip coordinates of each chip in the wafer coordinate system 34 is represented by (xmn0, ymn0), where m and n represent a position of a chip on the wafer represented by a row and a column. In this manner, the wafer coordinate system 34 and the chip coordinate system 35 are associated with each other by X=x+xmn0 and Y=y+ymn0.

Accordingly, when a defect point (defect coordinates) is represented in the wafer coordinate system 34 (X, Y), expression in the chip coordinate system 35 (x, y) can be obtained by subtracting the origin of the chip coordinates of each chip (xmn0, ymn0). More specifically, defect coordinates on a chip are represented as (x, y)=(X−xmn0, Y−ymn0) by using defect coordinates on the wafer. By performing the process for defect points of each chip of the target wafer, the superposition of wafer defect coordinates per chip (for all chips) at S3 can be achieved.

In FIG. 3, by overlaying origins of chip coordinates in two chips on the wafer 30, for example, chips 31 and 32, the result of overlaying the wafer defect coordinates is shown as a chip 37 (defect coordinates per chip after superposition) on the right side. Note that individual defect coordinates (defect points) are each represented by a cross mark (x). Although only the superposition result of two chips is shown in FIG. 3, the results of the process at S3 can be obtained by overlaying the origins of chip coordinates of all chips of the wafer. The process results are once stored in the information storage 13 or the like.

Although the superposition per chip has been described above, superposition may be performed per any other unit. For example, when a plurality of chips are collectively exposed with one shot which is a unit of exposure process, shot superposition (superposing process per shot) may be performed in place of the chip superposition (superposing process per chip) at S3 described above. This case may be considered as replacing the chip coordinate system 35 with a shot coordinate system.

<Process Flow (HS Detection)>

On the other hand, in FIG. 2, in parallel with the chip superposition (S3) of the defect coordinates (D1) outputted from the visual inspection tool 101, HS positions where defects due to lithography tend to occur are calculated (S4) by a simulation (litho simulation) of lithography (exposure process, mask and the like) by the litho simulator 102. Then, the HS coordinates (D2) are read into the information processing unit 10 (S5).

Subsequently, at S6, a process (first process) of grouping the read HS coordinate points based on the pattern layouts (D3) (their similarity) at the HS coordinate points (near these points) is performed. The data (D3) regarding pattern layout for use at this time is read from the pattern layout data server 103 into the information processing unit 10 as described above.

<Process Flow (First Classifying Process)>

Figure 4A:
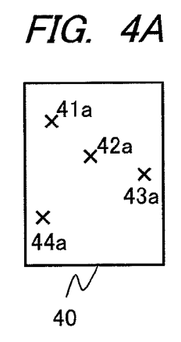
FIG. 4 is a drawing for describing a first classifying process (S6) of grouping HS based on similarity of pattern layout in the first process flow.

The process of S6 will be described with reference to FIG. 4. FIG. 4A depicts an example of one chip 40. A cross mark (x) at each of {41a, 42a, 43a, 44a} denotes a point (HS coordinate point) calculated (estimated) as an HS by the simulation (S4) in the chip 40.

Figure 4B:
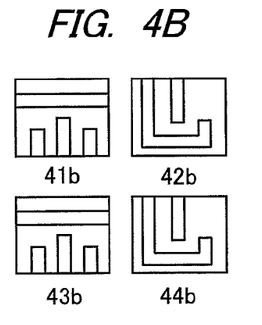

Also, in FIG. 4B, {41b, 42b, 43b, 44b} denote pattern layouts at the points {41a, 42a, 43a, 44a} in FIG. 4A, respectively. As illustrated, 41b and 43b have the same pattern layout (sufficiently high similarity), and 42b and 44b have the same pattern layout (sufficiently high similarity). In this process (S6), based on this similarity of pattern layout, the plurality of HS coordinate points are divided into two groups of {41a, 43a} and {42a, 44a} (classification of the HS coordinate points based on similarity of pattern layout).

Figure 4C:
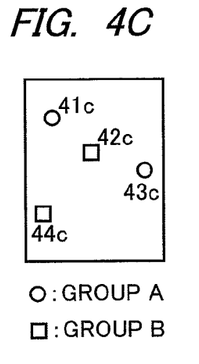

Also, in FIG. 4C, the results of grouping are represented as groups (classifications) A and B in which the points {41a, 43a} in the group A are represented as {41c, 43c} each with a circle mark (○) and points {42a, 44a} in the group B are represented as {42c, 44c} each with a square mark (□). Although there are two types of groups (classifications) A and B in this example, there can be plural (n) groups (classifications).

If the information regarding similarity (sameness) of circuit pattern layout used above can be obtained from the litho simulator 102, that information is used. In general, pattern layout information is retained also in the litho simulator 102 and is used for the simulation computation, and therefore that information can be obtained in this case. If the information cannot be obtained from the litho simulator 102, the information processing unit 10 takes or creates the information regarding the similarity of pattern layouts by using the data (D3) from the pattern layout data server 103, thereby performing the grouping based on similarity (S6).

In the process regarding the determination of similarity at S6, for example, the pattern layout (for example, the pattern layout near the HS coordinate point 41a) is converted to a line drawing as depicted by, for example, the pattern layout 41b (binary image information (bitmap)) of FIG. 4B. Then, regarding the images corresponding to the respective HS coordinate points, a computation for taking an image difference between two images is performed, and when the difference value is equal to or smaller than a predetermined threshold, these two images (corresponding two HS coordinate points) are determined as being identical in pattern layout (having sufficiently high similarity). By making the determinations in the same manner for the respective HS points, grouping is performed. The process results are once stored in the information storage 13 or the like.

<Process Flow (Comparison and Matching)>

Subsequently, at S7 of FIG. 2, the information processing unit 10 performs a process of superposition (overlaying for comparison and matching) by using the information data of the process results at steps S3 and S6 described above. At S7, a process is performed in which the HS coordinates (data of defect coordinates of each group in a region with a size of each chip) grouped (classified) based on the pattern layout (similarity) of the HS coordinate points on the chip at S6 are superposed on the results of chip superposition of the wafer defect coordinates at S3 (data of defect coordinates in a region with the size of each chip).

Then, at S8, it is determined whether the defect coordinates subjected to chip superposition (results at S3) are near the grouped HS coordinate points (results at S6) by using the results of S7. Regarding a defect point determined as being near the HS (Y) at S8 (near-HS defect point: K1), the defect point is sent to a process at S10 as a first grouping (G1). Regarding a defect point determined as not being near the HS (N) at S8 (non-near-HS defect point: K2), the defect point is sent to a process at S9 as a second grouping (G2) in order to check whether any HS occurs at a position (coordinates) that have not been expected (detected) in the simulation at S4. In the processes at S7 and S8, a process of comparing and matching the two types of data (detected defect and HS) with each other to discriminate the defect point is performed.

Figure 5A:
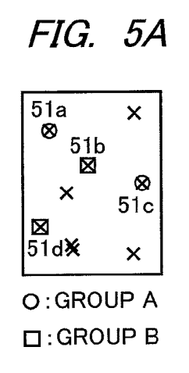
FIG. 5 is a drawing for describing a process (S7) of discriminating between near-HS defect points and non-near-HS defect points in the first process flow.

FIG. 5 depicts the state of the processes at S7 and S8 described above. FIG. 5A depicts the results of superposing the grouped HS coordinate points (results at S6) on the chip-superposed defect coordinates (results at S3) at S7. By way of example, the chip-superposed defect coordinates (results at S3) are identical to those of the chip 37 in FIG. 3. Also, the grouped HS coordinates (results at S6) are identical to those in FIG. 4C.

Figure 5B:
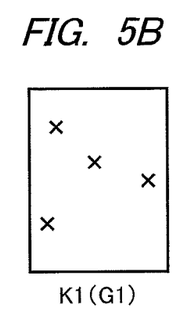
Figure 5C:
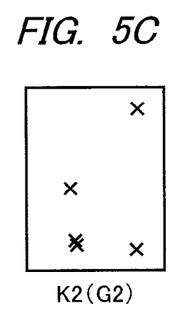

Furthermore, FIG. 5B depicts defect points (group of K1 (G1)) near HS points of each group (those of the group A (○) and the group B (□)) regarding the coordinate points (groups) of FIG. 5A in the determination at S8, and FIG. 5C depicts defect points (group of K2 (G2)) away from (not near) these HS points.

<Process Flow (Second Classifying Process)>

At S9 of FIG. 2, the information processing unit 10 performs a process (second classifying process) of grouping based on the pattern layouts (their similarity) at the coordinates of the non-near-HS defect points K2 that are the results of S8. By this means, at S9, HS (defect points) occurring at positions (coordinates) not expected (detected) in the simulation at S4 are also checked and detected as candidates for systematic defects due to exposure process or the like. The data (D3) regarding pattern layout for use at this S9 is read from the pattern layout data server 13 into the information processing unit 10 as described above.

Figure 6A:
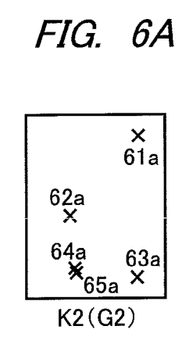
FIG. 6 is a drawing for describing a second classifying process (S9) of grouping the non-near-HS defect points based on similarity of pattern layout in the first process flow.
Figure 6B:
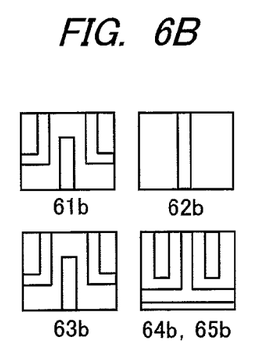

The process at S9 will be described with reference to FIG. 6. In the information depicted in FIG. 6A, {61a, 62a, 63a, 64a, 65a} representing defect points are defect points (K2) determined as not being near the HS, and are identical to those depicted in FIG. 5C. Also, {61b, 62b, 63b, 64b, 65b} which are pattern layouts (images) depicted in FIG. 6B represent the pattern layouts (their similarity) at the respective points {61a, 62a, 63a, 64a, 65a} of FIG. 6A. As illustrated, 61b and 63b are pattern layouts similar to each other, and 64b and 65b are pattern layouts similar to each other. Based on this, the HS points (K2) are grouped (classified) into two groups of {61a, 63a} and {64a, 65a}. Also, 62b (62a) is excluded from the candidates for detection at S9 because there is no other point having a similar circuit pattern layout. Grouping at S9 (determination and evaluation of similarity of pattern layouts) can be achieved by, for example, comparison and determination of the difference in a line drawing based on a threshold in the same manner as that at S6 described above.

Figure 6C:
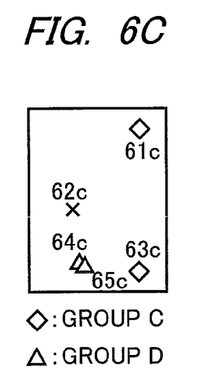

In FIG. 6C, the results of grouping are represented as groups (classifications) C and D in which points {61a, 63a} of the group C are represented as {61c, 63c} each with a diamond mark (◇) and points {64a, 65a} of the group D are represented as {64c, 65c} each with a triangle mark (△). The point 62a to be excluded from the candidates is represented as 62c with a cross mark (×).

<Process Flow (Map Development)>

Next, at S10 of FIG. 2, the information processing unit 10 performs a process in which the results at S8 and S9, that is, the grouped near-HS defect points K1 (G1) and the grouped non-near-HS defect points K2 (G2) are developed to a wafer map (defect coordinate distribution on the wafer) for each of the classified groups (A to D and others) of these defect points (groups). At S10, the grouped near-HS defect points K1 (G1) are defect points (groups) belonging to the groups A and B depicted in FIG. 5A. Also, the grouped non-near-HS defect points K2 (G2) are defect points (groups) belonging to the groups C and D depicted in FIG. 6C.

Figure 7:
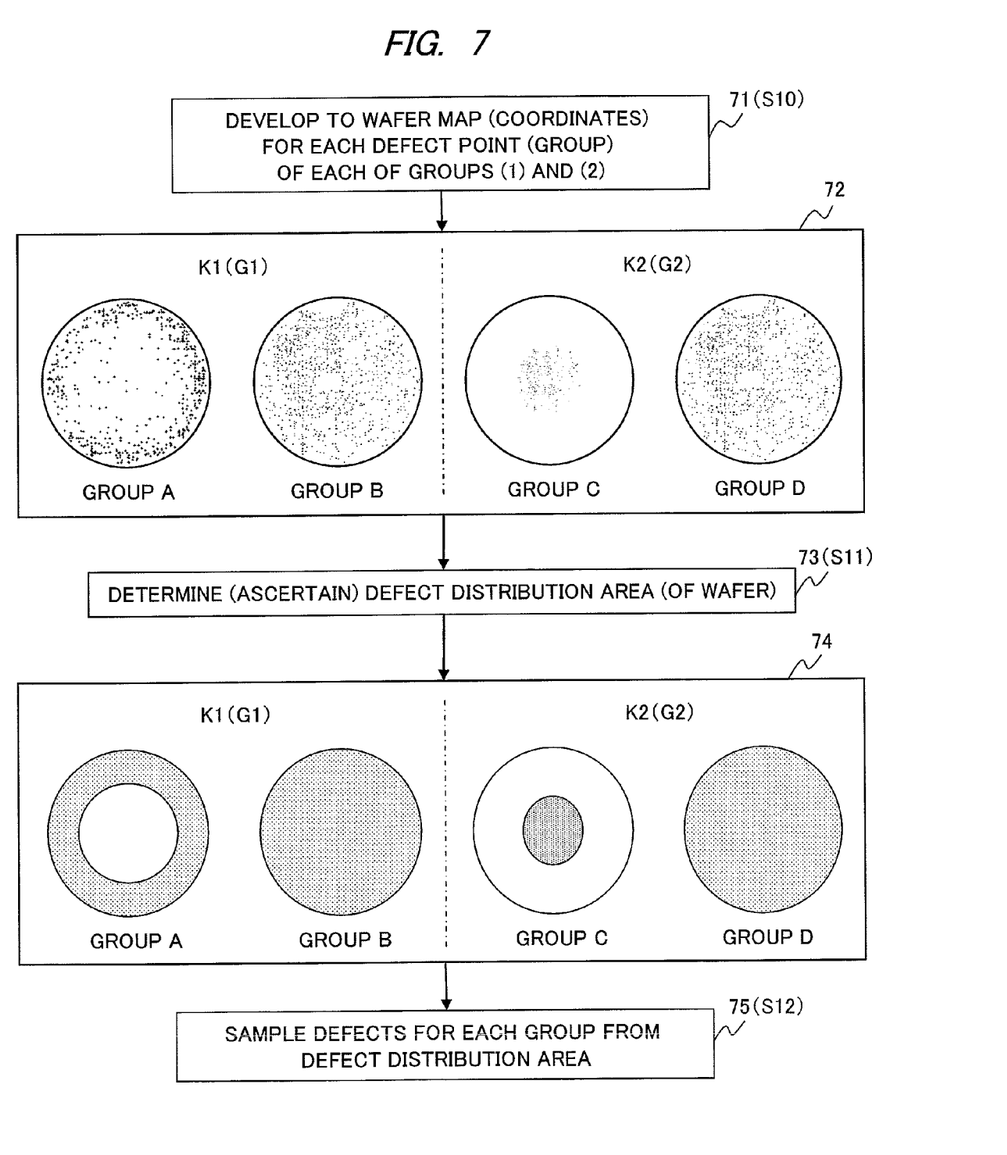
FIG. 7 is a drawing for describing a process (S11) of ascertaining a distribution area of defect points on a wafer in the first process flow.

In FIG. 7, 71 denotes a process of developing the defect points (groups) of each of the groups (G1 (A, B) and G2 (C, D)) at S10 to the wafer map (coordinates). Also, 72 denotes a schematic configuration obtained as a result by developing the defect points (groups) of the group G1 (A, B) and the group G2 (C, D) in the above-described example to the wafer map.

In this map development, since which chip each defect point belongs to has been known in advance from the data, the wafer coordinates of each defect point can be obtained by adding the origin of the chip coordinates represented by the wafer coordinates (34) to the chip coordinates (35) of each defect point described above. Also, when the shot superposition (per shot) is applied in place of the chip superposition (per chip) as described above, since which shot each defect point belongs to has been known similarly in advance from the data, the wafer coordinates of each defect point can be obtained by adding the origin of shot coordinates represented by the wafer coordinates to the shot coordinates of each defect point.

<Process Flow (Defect Distribution Area)>

At S11 of FIG. 2, the information processing unit 10 performs a process in which a distribution area of the defect points in a wafer area (per wafer) (pattern of uneven distribution thereof) is determined (ascertained) for each of the groups (A to D) based on the results at S10 (defect points (groups) in the wafer map denoted by 72). 73 of FIG. 7 denotes the process thereof, and 74 denotes the results thereof (ascertained defect distribution area of each of the groups (A to D)). As in this example, it can be found that the area where the defects are present on each wafer is varied for each of the groups A, B, C, and D (uneven distribution). The reason for this is that an area where HS actually becomes a defect is affected by the influence of topography (characteristics) of the surface of the wafer.

In the example denoted by 74, a shape (pattern of uneven distribution) of a defect distribution area in a wafer area (circular shape) in each group is as follows. The group A is a pattern in which a density is large near the circumference. The groups B and D are patterns in which defects are distributed over its entirety. The group C is a pattern in which a density is large near the center.

As an example of a method of determining a defect distribution area at S11 (73), a method in which a portion with a large density is ascertained as a distribution area is known. For example, Non-Patent Document 2 can be applied.

<Process Flow (Sampling)>

Then, at S12 of FIG. 2, the information processing unit 10 performs a process of sampling a defect (review target defect) for each of the groups (A to D) for the results at S11 (defect distribution area as denoted by 74). 75 of FIG. 7 denotes the process thereof.

As an example of the method of sampling a defect from the ascertained area at S12 (75), a sampling method in a spatially random manner or a sampling method in a random manner for the sequence in which the defect information is stored is known.

Next, at step S13, the information processing unit 10 transfers, to the defect review tool 104, information data about the defect points (review target defects) sampled at S12 together with information data indicating distribution areas (74 or the like) where the defect points are sampled (defect distribution area information) as process result information (reviewed defect coordinate data: D4). In the defect review tool 104, processes such as outputting (screen display) of the information to the output device 105 and reviewing thereof can be performed by using the information data (D4).

Modification Example

Second Process Flow

Figure 8:
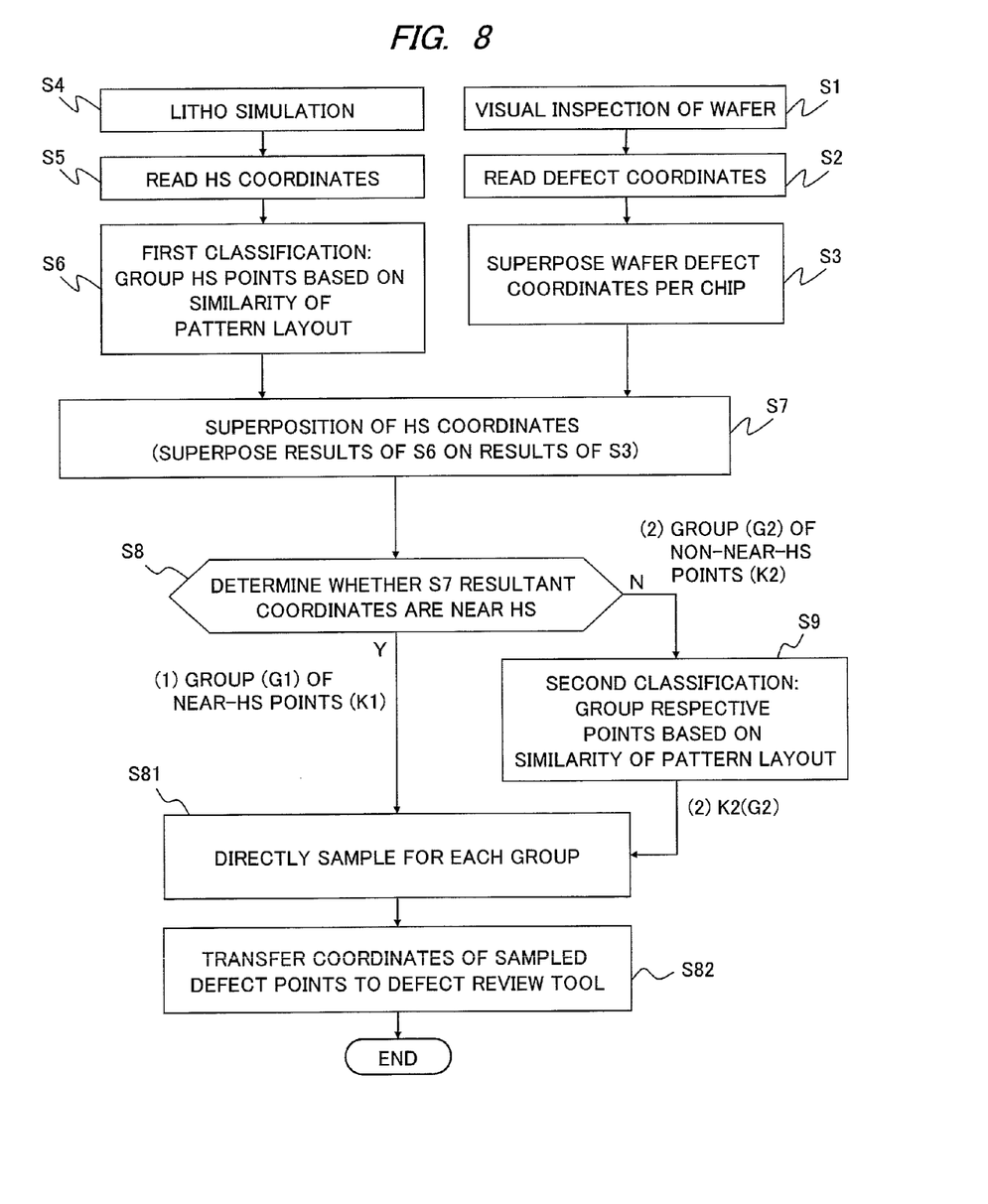
FIG. 8 is a drawing showing a process flow (second process flow) of a modification example according to the first embodiment.

A second process flow will be described as a modification example of the first embodiment. In the second process flow depicted in FIG. 8, processes denoted as S81 and S82 are characteristic, in which sampling is directly performed for each of the grouped near-HS defect points (K1) and the grouped non-near-HS defect points (K2). S1 to S9 of FIG. 8 are similar processes as those of FIG. 2. In the case of the second process flow, a sampling method without performing the process like that at S11 (determination of a defect distribution area) (that is, without applying an area (pattern) like 74 of FIG. 7) is used, and a set of defects to be sampled is different.

At S81, defect points are sampled for each of the grouped near-HS points (group G1 of K1, each classification group) and the grouped non-near-HS points (group G2 of K2, each classification group). As an example of the sampling method at this time, a sampling method in a spatially random manner or a sampling method in a random manner for the sequence in which the defect information is stored is known. Also, a method in which a chip, a shot, or an area to be sampled is defined in advance and sampling is performed from defect points in that area may be applicable. At S82, process result information such as the coordinates of the defect points sampled at S81 is transferred to the defect review tool 104.

Modification Example

Third Process Flow

Figure 9:
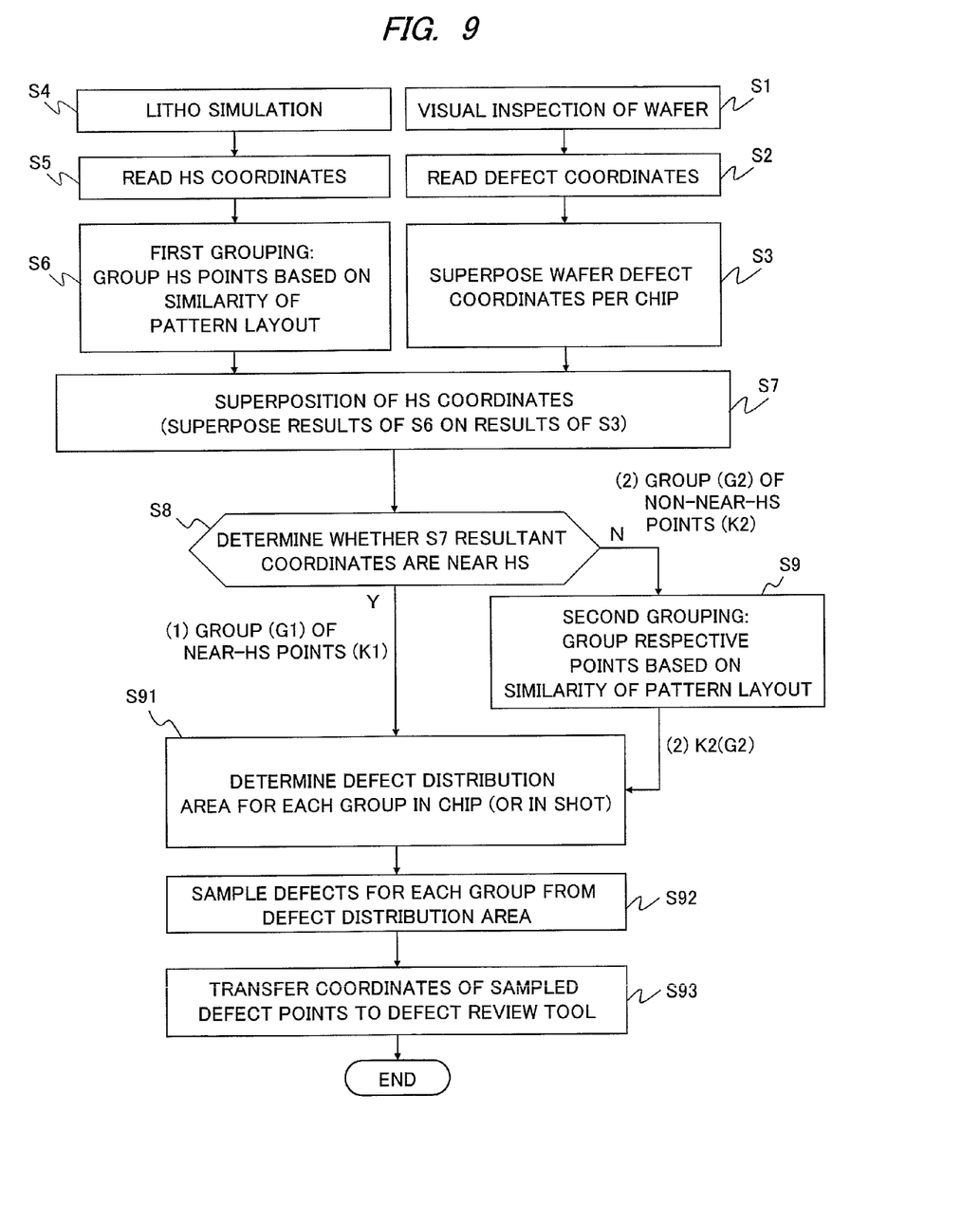
FIG. 9 is a drawing showing a process flow (third process flow) of a modification example according to the first embodiment.

A third process flow will be described as a modification example of the first embodiment. In the third process flow depicted in FIG. 9, processes denoted as S91 and S92 are characteristic, in which a distribution state of the defect points is analyzed (distribution area is determined) for each of the grouped near-HS defect points (K1) and the grouped non-near-HS defect points (K2) while keeping the state of chip superposition, shot superposition, or the like, thereby ascertaining an area to be sampled. S1 to S9 of FIG. 9 are identical processes to those of FIG. 2. In the third process flow, the process at S11 is different, in which the target of the process is not a wafer but a chip superposition and the like.

Defect distribution analysis per chip is performed in view of the fact that surface asperities occur by the influence of pattern density or under layer and affect the occurrence of a defect at an HS. Also, defect distribution analysis per shot is performed in view of the possibility of occurrence of a defect at an HS due to aberration such as field curvature in a lithography tool in addition to the reason described above.

At S91, a distribution state of the defect points is determined (ascertained) per chip or per shot for each of the grouped near-HS defect points (group G1 of K1, each classification group) and the grouped non-near-HS defect points (group G2 of K2, each classification group), thereby ascertaining a defect sampling area. Subsequently, at S92, defect points are sampled in the ascertained sampling area. As an example of the sampling method at this time, a sampling method in a spatially random manner or a sampling method in a random manner for the sequence in which the defect information is stored is known similarly to the above. At S93, process result information such as the coordinates of the sampled defect points is transferred to the defect review tool 104.

Second Embodiment

Next, a system of the second embodiment of the present invention will be described with reference to FIGS. 10 to 12. The defect review tool and method according to the second embodiment have means and process step of reviewing a selected defect (reviewed defect) in addition to the reviewed defect selection processing tool and method described above and represent a defect review tool 140 of FIG. 10 and a system (semiconductor inspection system) 200 including the defect review tool, and a method executed by the tool.

<Tool Configuration (2)>

Figure 10:
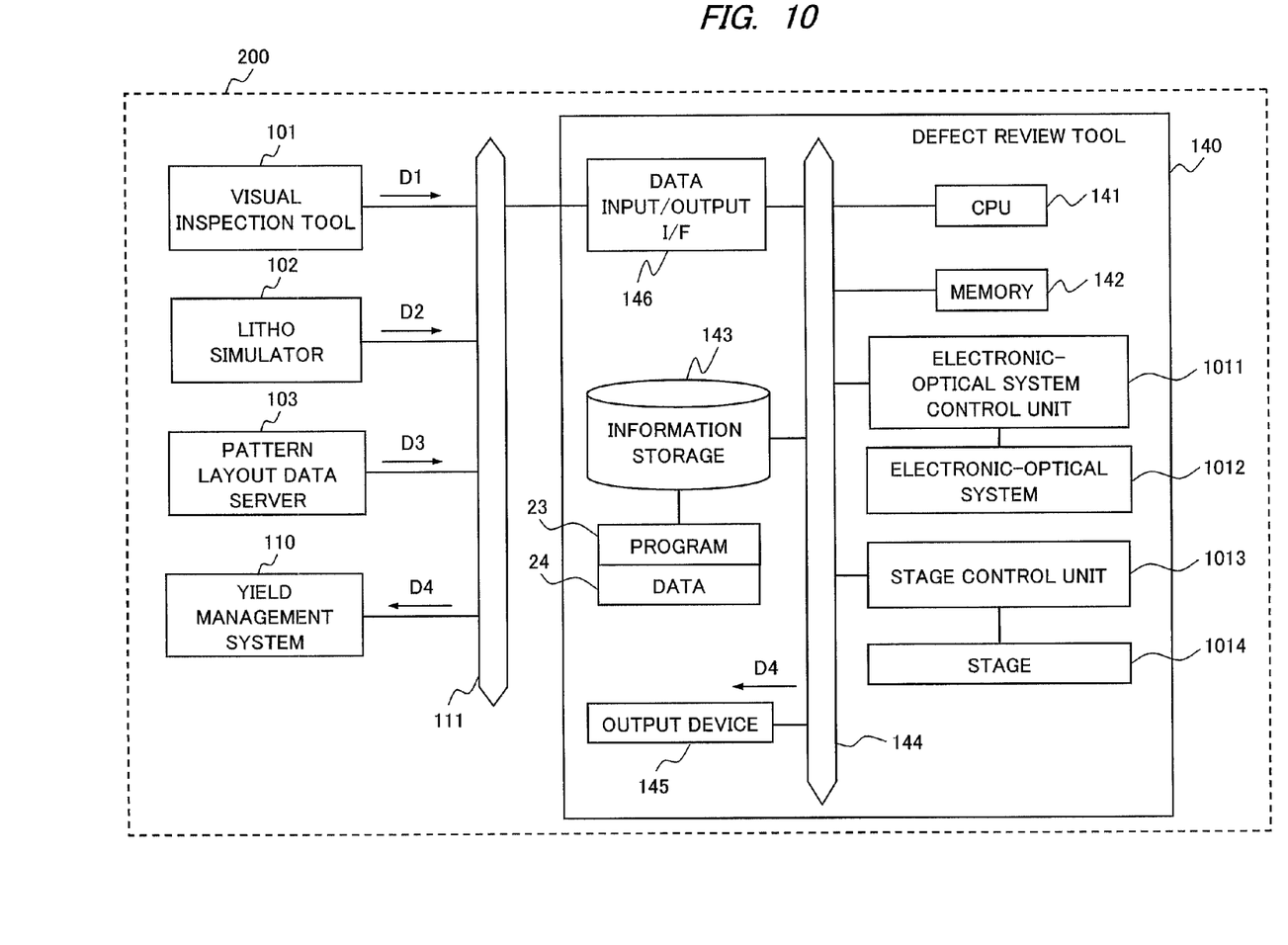
FIG. 10 is a drawing showing a system configuration according to the second embodiment of the present invention.

FIG. 10 depicts a tool configuration of the present system (semiconductor inspection system) 200. A main device of the system 200 is the defect review tool 140, and a visual inspection tool 101, a litho simulator 102, a pattern layout data server 103, a yield management system 110, and others are connected to the defect review tool 140 via a LAN 111. The second embodiment can be regarded as the defect review tool 140 including the functions of the information processing unit 10 described in the first embodiment.

Information (D1, D2, and D3) outputted from devices similar to those described above (FIG. 1) such as the visual inspection tool 101, the litho simulator 102, and the pattern layout data server 103 is inputted directly to the defect review tool 140 or is inputted to the defect review tool 140 via the yield management system 110.

The defect review tool 140 performs communication with outside via a data input/output IF 146. In the defect review tool 140, a CPU 141, a memory 142, an information storage (HDD or the like) 143, an output device 145, the data input/output I/F 146, an electronic-optical system control unit 1011, a stage control unit 1013, and others are connected via a bus 144. An electronic-optical system 1012 is activated by an instruction from the CPU 141 via the electronic-optical system control unit 1011. Also, a stage 1014 is activated by an instruction from the CPU 141 via the stage control unit 1013. The defect review tool 140 performs imaging by using the devices from the electronic-optical system control unit 1011 to the stage 1014.

The yield management system 110 performs processes such as those of accumulating defect detection data (D1) and offering and managing various statistical data information for a human to estimate the yields predicted from the accumulated data.

Processes to be performed by the CPU 141 having the information (D1, D2, and D3) from each of the external devices (101, 102, and 103) as inputs are basically similar to those shown in the first embodiment (first process flow) (corresponding program 23 and data 24 are used). Information (D4) of sampled defect coordinates which is the process results from the CPU 141 is recorded on the memory 142, the information storage 143, or others. The defect review tool 140 positions the stage 1014 and takes images of defects by using the recorded defect coordinates.

<Operation Sequence>

Figure 11:
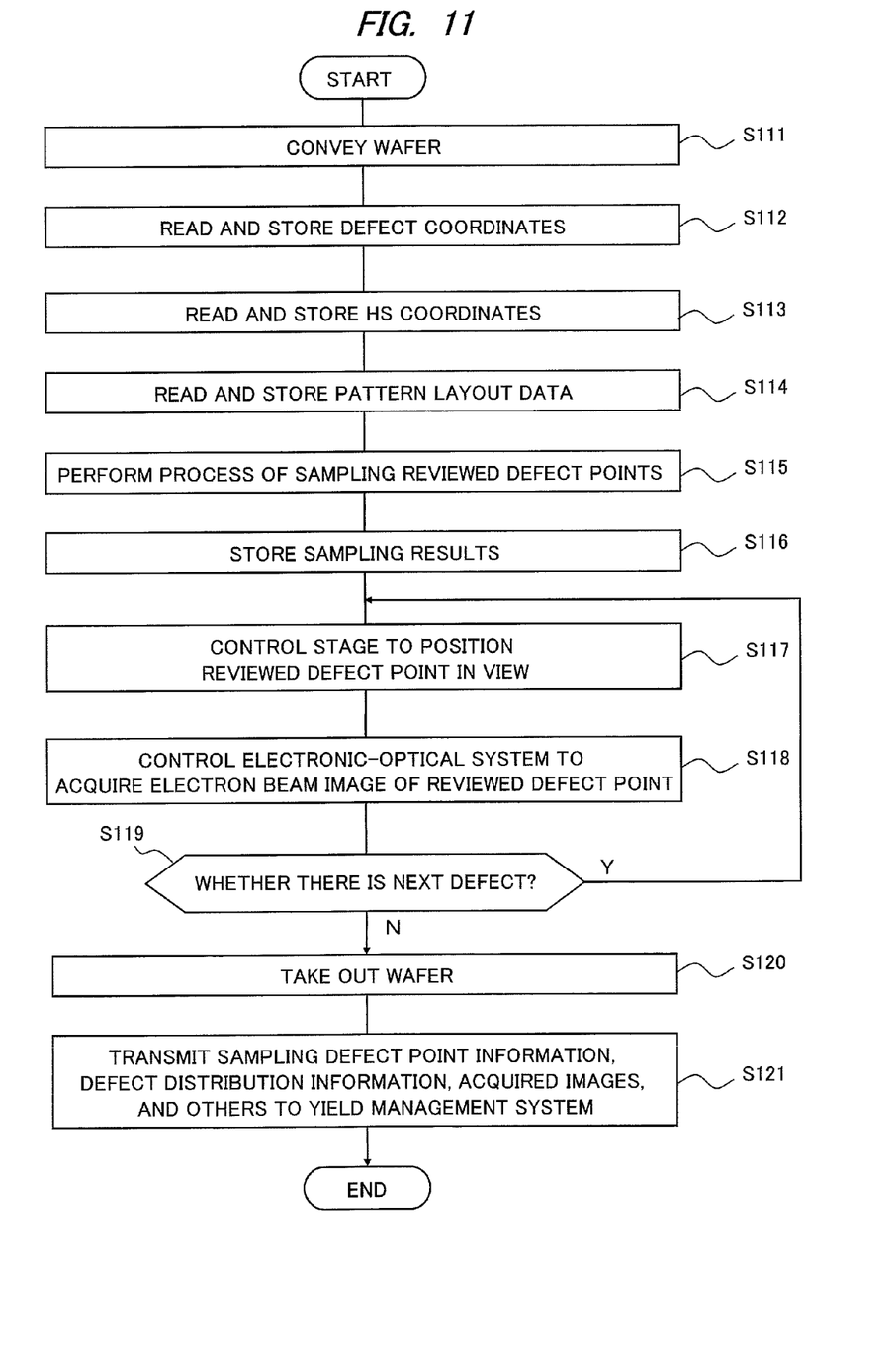
FIG. 11 is a drawing showing a schematic flow of an imaging operation sequence in the second embodiment.

FIG. 11 depicts a schematic flow of an operation sequence of this imaging (acquisition of reviewed defect image). First, a target wafer is conveyed in the defect review tool 140 (S111). Subsequently, in the defect review tool 140, defect coordinates are read and stored in the storage (142 or 143 of FIG. 10) in the tool (S112), and HS coordinates are similarly read and stored (S113). Finally, pattern layout data is similarly read and stored (S114). The sequence of reading data at S112 to S114 may not be as described above. After the data is read, the process of sampling the defects (review target defects) described in the first embodiment is performed (S115), and information about the coordinates of the sampled defects which are the process results is stored in the storage in the tool (S116).

Next, in the defect review tool 140, the defect coordinates are read in the sequence in which the defects are stored, the stage 1014 is controlled through the stage control unit 1013, and a reviewed defect point is positioned in the view of the electronic-optical system 1012 through the electronic-optical system control unit 1011 (S117). After positioning, an electron beam image of the defect is acquired (S118). If there is still a defect to be reviewed, the process returns to S117. If there is no other defect to be reviewed, the wafer is taken out (S120).

Finally, information data such as (1) information about the sampled defect points, (2) information about a defect distribution area, and (3) the acquired (imaged) images (defect images) is transmitted to the yield management system 110 (S121) to end the process.

Display Example

Figure 12:
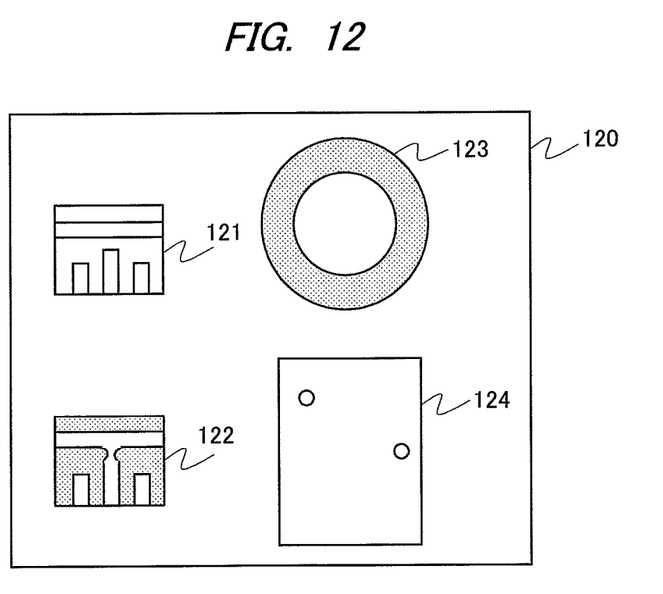
FIG. 12 is a drawing showing an example of display of process result information in the second embodiment.

FIG. 12 depicts an example of display of process information on a display screen of the tool of the second embodiment. In this example, on the display screen of the output device 145 or the like of the defect review tool 140, (1) the information about the sampled defect points (for example, position information such as coordinates in a chip (or a shot or the like)), (2) the information about the defect distribution area, (3) the information about the acquired (imaged) images (defect images or the like), and (4) pattern layout information (pattern layout data D3) described above are displayed. This information display may be performed not only by the defect review tool 140 but also by the yield management system 110 or the like.

120 denotes a display screen in the output device 145 or the like. 121 denotes, as (4) the pattern layout information, an image (line drawing) of an ideal (designed) pattern layout obtained by the search from the pattern layout data D3 at the defect point. 122 denotes, as (3) the acquired image information, a defect image (image of the pattern layout including a defective part (for example, short-circuit)) for the image 121. 123 denotes, as (2) the defect distribution area information, a distribution state (pattern of uneven distribution) of defects (groups) on the wafer which belong to the same group as that of the defect displayed in the defect image 122. 124 denotes, as (1) the sampling defect point position information, coordinates or the like (circle marks) where defects of the same group occur in a chip (or a shot or the like). Note that the same group refers to a set of defect points having the same (similar) pattern layout at the defect position as described above. Also, 124 represents the result of chip superposition (or shot superposition or the like).

Effects of the Embodiments and Others

As has been described in the foregoing, according to each of the embodiments, by matching (S7 and S8) the HS (S4 to S6) obtained in advance in a simulation and the defect points (S1 to S3) obtained as a result of the visual inspection with each other, a systematic defect occurring at the HS (systematic defect buried in many defects detected as the results of the visual inspection) can be reliably detected. Also, by acquiring an uneven distribution in a defect occurrence distribution on a wafer (S11 or others), a systematic defect occurring due to topography of the wafer can also be detected.

Further, in the configuration of the first embodiment, in particular, HS that cannot be found in advance by the computation of the litho simulator 102 (S4) can be extracted as candidates for systematic defects by the step S9 (second classifying process) which is a process step common to the process flows shown in FIGS. 2, 8, and 9.

Also, the information data regarding HS once extracted in the process at S9 is handled as known HS when a wafer having the same (similar) pattern layout is processed in the next and subsequent operations, thereby reducing the cost of the process at S9. More specifically, with using the circuit pattern layout extracted at S9 as a similar pattern layout for each group as a template, all the positions (coordinates) having the same circuit pattern layout are searched from the pattern layout data (D3) of the wafer, and a set of the positions (coordinates) is taken as one HS group. By handling these grouped HS in the same manner as the HS obtained at S4 to S6 (HS obtained by grouping the HS coordinate points read from the litho simulator 102 based on similarity of pattern layout at the relevant coordinate points), the computation load at S9 in the next and subsequent operations can be reduced.

When the process described above is to be performed, for example, the data about HS grouped at S9 is stored in the memory 12 or the like, and the data about the HS is reused at S6 (first classifying process) in a process flow of a wafer having a similar pattern layout in the next and subsequent operations. In this case, regarding the relevant defect point, the process is branched at S8 to the process of a near-HS defect point K1 (G1). Thus, the process as that of S9 is omitted, and therefore the entire process can be made efficient.

In the foregoing, the invention made by the inventors of the present invention has been concretely described based on the embodiments. However, it is needless to say that the present invention is not limited to the foregoing embodiments and various modifications and alterations can be made within the scope of the present invention.

INDUSTRIAL APPLICABILITY

The present invention can be used for semiconductor manufacturing and inspecting systems and others.

DESCRIPTION OF REFERENCE NUMERALS 10 information processing unit
11 CPU
12 memory
13 information storage (HDD or the like)
14 bus
15 defect coordinate input I/F
16 Hot Spot coordinate input I/F
17 pattern layout data input I/F
18 data output I/F
21 program
22 data
23 program
24 data
30 wafer
31, 32, 36, 37 chip
34 wafer coordinates (system)
35 chip coordinates (system)
40 chip
71, 73, 75 process
72 wafer map
74 defect distribution area
100, 200 semiconductor inspection system
101 visual inspection tool
102 litho simulator
103 pattern layout data server
104 defect review tool
105 output device
110 yield management system
111 LAN
120 display screen
121 pattern layout information
122 acquired image information
123 defect distribution area information
124 sampling defect point position information
140 defect review tool
141 CPU
142 memory
143 information storage
144 bus
145 output device
146 data input/output I/F
1011 electronic-optical system control unit
1012 electronic-optical system
1013 stage control unit
1014 stage

The invention claimed is:
1. A reviewed defect selection processing method, in which based on information about a plurality of detected defects outputted from a visual inspection tool targeted for a semiconductor wafer, a process of selecting one or more reviewed defects for performing a detailed review from the plurality of detected defects is performed by using information processing of a computer, the method comprising:
a process step of inputting information about positions of the plurality of detected defects from the visual inspection tool;
a process step of inputting information about positions of hot spots of the wafer calculated by a litho simulator;
a process step of inputting pattern layout data on a circuit board of the wafer;
a process step of performing a first process of classifying the hot spots into groups based on similarity of pattern layout at the positions and inputting information about the positions of the hot spots of each classified group;
a process step of discriminating the plurality of detected defects between defects near the hot spots of the classified groups and defects not near the hot spots of the classified groups;
a process step of performing a first grouping of the defects near the hot spots for each of the classified groups of the hot spots and selecting, from the defects subjected to the first grouping, a reviewed defect for each of the classified groups; and a process step of performing a second process of classifying the defects not near the hot spots into groups based on similarity of pattern layout at the positions, performing a second grouping of the defects of each of the classified groups for each classified group, and selecting, from the defects subjected to the second grouping, a reviewed defect for each classified group.

2. The reviewed defect selection processing method according to claim 1, further comprising:

a process step of ascertaining a defect distribution area on the wafer for each of the classified groups in the first and second groupings; and a process step of selecting a reviewed defect from the ascertained area.

3. The reviewed defect selection processing method according to claim 1, further comprising:

a process step of ascertaining a defect distribution area on a chip or a shot of the wafer for each of the classified groups in the first and second groupings; and a process step of selecting a reviewed defect from the ascertained area.

4. The reviewed defect selection processing method according to claim 1, further comprising a process step of discriminating the detected defects between defects near the hot spots of the classified groups and defects not near the hot spots of the classified groups by representing the detected defects by coordinates on a chip or a shot of the wafer, representing the hot spots by coordinates on the chip or the shot, and comparing the coordinates of the detected defects with the coordinates of the hot spots.

5. A defect review method, in which based on information about a plurality of detected defects outputted from a visual inspection tool targeted for a semiconductor wafer, a process of selecting and reviewing one or more reviewed defects for performing a detailed review from the plurality of detected defects is performed by using information processing of a computer, the method comprising:

a process step of inputting information about positions of the plurality of detected defects from the visual inspection tool;

a process step of inputting information about positions of hot spots of the wafer calculated by a litho simulator;

a process step of inputting pattern layout data on a circuit board of the wafer;

a process step of performing a first process of classifying the hot spots into groups based on similarity of pattern layout at the positions and inputting information about the positions of the hot spots of each classified group;

a process step of discriminating the plurality of detected defects between defects near the hot spots of the classified groups and defects not near the hot spots of the classified groups;

a process step of performing a first grouping of the defects near the hot spots for each of the classified groups of the hot spots and selecting, from the defects subjected to the first grouping, a reviewed defect for each of the classified groups;

a process step of performing a second process of classifying the defects not near the hot spots into groups based on similarity of pattern layout at the positions, performing a second grouping of the defects of each of the classified groups for each classified group, and selecting, from the defects subjected to the second grouping, a reviewed defect for each classified group; and a process step of acquiring an image for performing a detailed review of the reviewed defect based on information about the selected reviewed defect.

6. The defect review method according to claim 5, further comprising:

a process step of ascertaining a defect distribution area on the wafer for each of the classified groups in the first and second groupings; and a process step of selecting a reviewed defect from the ascertained area.

7. The defect review method according to claim 5, further comprising:

a process step of ascertaining a defect distribution area on a chip or a shot of the wafer for each of the classified groups in the first and second groupings; and a process step of selecting a reviewed defect from the ascertained area.

8. The defect review method according to claim 5, further comprising a process step of discriminating the detected defects between defects near the hot spots of the classified groups and defects not near the hot spots of the classified groups by representing the detected defects by coordinates on a chip or a shot of the wafer, representing the hot spots by coordinates on the chip or the shot, and comparing the coordinates of the detected defects with the coordinates of the hot spots.

9. The defect review method according to claim 5, further comprising a process step of displaying, on a screen, the acquired image of the reviewed defect, information about a pattern layout at a position of the defect, and information indicating a defect distribution area on the wafer or on a chip or a shot in the classified group to which the defect belongs.

10. A reviewed defect selection processing tool, in which based on information about a plurality of detected defects outputted from a visual inspection tool targeted for a semiconductor wafer, a process of selecting one or more reviewed defects for performing a detailed review from the plurality of detected defects is performed by using information processing of a computer, the tool comprising:

a first input processing unit which inputs information about positions of the plurality of detected defects from the visual inspection tool;

a second input processing unit which inputs information about positions of hot spots of the wafer calculated by a litho simulator;

a third input processing unit which inputs pattern layout data on a circuit board of the wafer; and an information processing unit which performs a first process of classifying the hot spots into groups based on similarity of pattern layout at the positions and inputting information about the positions of the hot spots of each classified group, a process step of discriminating the plurality of detected defects between defects near the hot spots of the classified groups and defects not near the hot spots of the classified groups, a process step of performing a first grouping of the defects near the hot spots for each of the classified groups of the hot spots and selecting, from the defects subjected to the first grouping, a reviewed defect for each of the classified groups, and a process step of performing a second process of classifying the defects not near the hot spots into groups based on similarity of pattern layout at the positions, performing a second grouping of the defects of each of the classified groups for each classified group, and selecting, from the defects subjected to the second grouping, a reviewed defect for each classified group.

11. The reviewed defect selection processing tool according to claim 10,
wherein the information processing unit performs a process step of ascertaining a defect distribution area on the wafer for each of the classified groups in the first and second groupings, and
a process step of selecting a reviewed defect from the ascertained area.

12. The reviewed defect selection processing tool according to claim 10,
wherein the information processing unit performs a process step of ascertaining a defect distribution area on a chip or a shot of the wafer for each of the classified groups in the first and second groupings, and
a process step of selecting a reviewed defect from the ascertained area.

13. The reviewed defect selection processing tool according to claim 10,
wherein the information processing unit performs a process step of discriminating the detected defects between defects near the hot spots of the classified groups and defects not near the hot spots of the classified groups by representing the detected defects by coordinates on a chip or a shot of the wafer, representing the hot spots by coordinates on the chip or the shot, and comparing the coordinates of the detected defects with the coordinates of the hot spots.

14. A defect review tool, in which based on information about a plurality of detected defects outputted from a visual inspection tool targeted for a semiconductor wafer, a process of selecting and reviewing one or more reviewed defects for performing a detailed review from the plurality of detected defects is performed by using information processing of a computer, the tool comprising:
a first input processing unit which inputs information about positions of the plurality of detected defects from the visual inspection tool;
a second input processing unit which inputs information about positions of hot spots of the wafer calculated by a litho simulator;
a third input processing unit which inputs pattern layout data on a circuit board of the wafer; and
an information processing unit which performs a process step of performing a first process of classifying the hot spots into groups based on similarity of pattern layout at the positions and inputting information about the positions of the hot spots of each classified group,
a process step of discriminating the plurality of detected defects between defects near the hot spots of the classified groups and defects not near the hot spots of the classified groups,
a process step of performing a first grouping of the defects near the hot spots for each of the classified groups of the hot spots and selecting, from the defects subjected to the first grouping, a reviewed defect for each of the classified groups,
a process step of performing a second process of classifying the defects not near the hot spots into groups based on similarity of pattern layout at the positions, performing a second grouping of the defects of each of the classified groups for each classified group, and selecting, from the defects subjected to the second grouping, a reviewed defect for each classified group, and
a process step of acquiring an image for performing a detailed review of the reviewed defect based on information about the selected reviewed defect.

15. The defect review tool according to claim 14,
wherein the information processing unit performs a process step of ascertaining a defect distribution area on the wafer for each of the classified groups in the first and second groupings, and
a process step of selecting a reviewed defect from the ascertained area.

16. The defect review tool according to claim 14,
wherein the information processing unit performs a process step of ascertaining a defect distribution area on a chip or a shot of the wafer for each of the classified groups in the first and second groupings, and
a process step of selecting a reviewed defect from the ascertained area.

17. The defect review tool according to claim 14,
wherein the information processing unit performs a process step of discriminating the detected defects between defects near the hot spots of the classified groups and defects not near the hot spots of the classified groups by representing the detected defects by coordinates on a chip or a shot of the wafer, representing the hot spots by coordinates on the chip or the shot, and comparing the coordinates of the detected defects with the coordinates of the hot spots.

18. The defect review tool according to claim 14,
wherein the information processing unit performs a process step of displaying, on a screen, the acquired image of the reviewed defect, information about a pattern layout at a position of the defect, and information indicating a defect distribution area on the wafer or on a chip or a shot in the classified group to which the defect belongs.

* * * * *